United States Patent [19]

Finizio

[11] 3,959,300

[45] May 25, 1976

[54] NOVEL INDOLOBENZAZEPINE DERIVATIVES, USEFUL AS TRANQUILIZERS

[75] Inventor: Michael Finizio, Howard Beach, N.Y.

[73] Assignee: Endo Laboratories, Inc., Garden City, N.Y.

[22] Filed: June 14, 1974

[21] Appl. No.: 479,512

Related U.S. Application Data

[60] Division of Ser. No. 170,990, Aug. 11, 1971, Pat. No. 3,764,684, and a continuation-in-part of Ser. No. 389,197, Aug. 17, 1973, abandoned.

[52] U.S. Cl. .................. 260/296 P; 260/296 A; 424/263
[51] Int. Cl.² ........................................ C07D 221/02
[58] Field of Search ............... 260/296 P, 296 A

[56] References Cited

UNITED STATES PATENTS

| 3,764,684 | 10/1973 | Finizio .......................... 424/263 |
| 3,829,431 | 8/1974 | Berger et al. ................ 260/294.8 A |

*Primary Examiner*—John D. Randolph

[57] ABSTRACT

Certain novel 1,2,3,4,8,9-hexahydro-3-(substituted)pyrido[4',3':2,3]indolo[1,7-ab][1]-benzazepines are useful as minor tranquilizers (anxiolytics) and/or major tranquilizers (antipsychotics). The minor tranquilizers are effective at non-ataxic doses, and are not likely to cause addiction when abused. A representative compound in this class is 3-(cyclopropylmethyl)-1,2,3,4,8,9-hexahydropyrido[4',3':2,3]indolo[1,7-ab][1]benzazepine.

12 Claims, No Drawings

NOVEL INDOLOBENZAZEPINE DERIVATIVES, USEFUL AS TRANQUILIZERS

CROSS REFERENCE TO RELATED APPLICATION

This application is a divisional of my copending application Ser. No. 170,990, filed August 11, 1971 now U.S. Patent 3,764,684 granted October 9, 1973 and a continuation-in-part of my copending application U.S. Ser. No. 389,197, filed Aug. 17, 1973 now abandoned.

BACKGROUND OF THE INVENTION

This invention relates to novel indolobenzazepine derivatives, which are useful as either minor tranquilizers (anxiolytics) or as major tranquilizers (antipsychotics), or as both.

Iminodibenzyl can be named according to the IUPAC 1957 Rules 10,11-dihydro-5H-dibenz[b,f]azepine. This compound was described by Thiele and Holzinger as early as 1899 [Ann. Chem 305, page 100]. These authors also reported nitrosation of the iminodibenzyl and formation of N-nitroso iminodibenzyl [ibid, 102]. Certain benzazepino-pyrido-indole derivatives have been described in U.S. Pat. Nos. 3,373,153; 3,373,154; 3,373,168; and 3,457,271. The last named patent describes 11-(lower alkyl)hexahydro-1- benzazepino[3,2,1-h,i]pyrido[4,3-b]indoles, which are intermediates to 11-(lower alkyl)octahydrobenzazepino[3,2,1-h,i]pyrido[4,3-b]indoles. The octahydro compounds are antidepressants. These compounds can be represented by the generic formula (1)

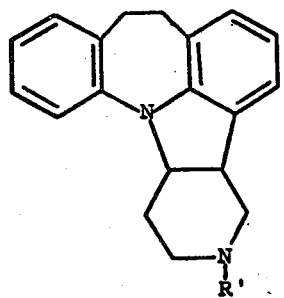

(1)

where ' is a straight or branched-chain alkyl having 1-7 carbon atoms.

South African patent No. 680,169 discloses a group of benzazepino-pyrido-indole derivatives of formula (2), which possess a "marked depressant activity on the central nervous system and are useful as sedatives and tranquilizers."

R'' is hydrogen or a straight chain alkyl group of no more than 4 carbon atoms.

The South African patent does not describe more closely the type of depressant activity of these novel compounds.

General, nonselective central nervous system depressants are one class of drugs well recognized in the art [L.S. Goodman and A. Gilman (Eds.), The Pharmacologic Basis of Therapeutics, 4th Ed., The Macmillan Co., N.Y., 1970]. Included in this category are anesthetic gases and vapors, aliphatic alcohols and the barbiturates and related sedativehypnotic drugs. These agents share the common property of depressing all excitable tissue.

Also well recognized in the art is another class of depressant drugs known as selective central system depressants [ibid, page 40]. In contrast to the nonselective depressants, these drugs selectively affect particular central nervous system functions. Included in this category are major tranquilizers such as the phenothiazines, and minor tranquilizers exemplified by the benzodiazepines. The former, also known as antipsychotics, are used mainly in schizophrenia and other psychoses, while the latter, also known as anxiolytics, are effective in behavioral states characterized by anxiety and tension.

Most commonly used drugs, whether minor tranquilizers or major tranquilizers have undesirable side effects, including ataxia and physical dependence. There often also are undesirable pharmacological side effects which limit their usefulness, such as jaundice, parkinsonism, dyskinesia, faintness, palpitation, dry mouth, and so on.

There is, therefore, a need in the art for additional psychotherapeutic agents which would have fewer side effects than those used today and which would be effective for the treatment of either neuroses or psychoses.

SUMMARY OF THE INVENTION

According to this invention, it has now been discovered that certain substituted hexahydropyridoindolobenzazepines and their salts with pharmaceutically acceptable organic or inorganic acids are effective psychotropic agents. Certain compounds within this class have both minor and major tranquilizer activity. At the dosage used, the minor tranquilizers of this series do not appear to have narcotic effects, and they do not cause ataxia. The novel compounds of the present invention can be represented by the generic formula (3), below:

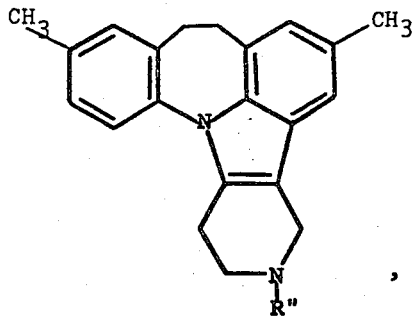

(2)

, where

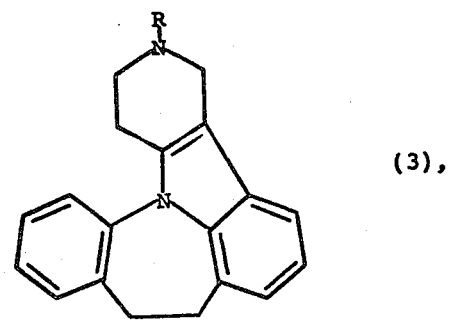

(3), where R is represented by the formula $C_n(H_{2n-x})Z_y$, where Z is oxygen or sulfur; n is a positive integer of 3–12; x is 1, 3 or 5; and y is 0 or 1; with the proviso that when y is 1, n is no larger than 6, and x is 1; and when x is 5, n is at least 7.

This invention also relates to pharmaceutical preparations containing the active compounds of the present invention, as well as to methods of producing either anxiolytic or antipsychotic effects in warm-blooded animals by administering to a warm-blooded animal the novel compounds of the present invention or their salts.

DETAILED DESCRIPTION OF THE INVENTION

The novel compounds of this invention are named according to the IUPAC 1957 Rules as 3-substituted derivatives of 1,2,3,4,8,9-hexahydropyrido[4', 3':2,-3]indolo[1,7-ab][1]-benzazepine, according to the numbering system indicated below:

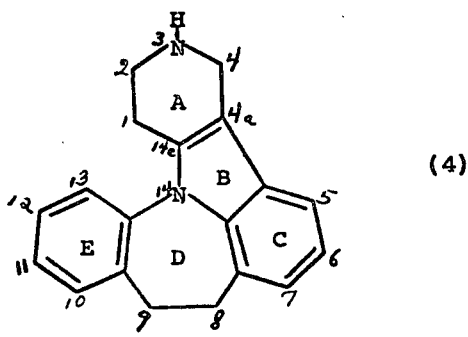

(4)

wherein rings E and D form the benzazepine portion of the molecule; rings B and C form the indolo portion; and ring A forms the pyrido portion.

The substituent R in formula (3) can be, for example, (cycloalkyl)alkyl, (alkylcycloalkyl)alkyl, straight chain or branched alkenyl, alkadienyl or alkynyl, (cycloalkenyl)alkyl, (cycloalkadienyl)alkyl, (oxacycloalkyl)alkyl, (thiacycloalkyl)alkyl, (bicycloalkyl)alkyl, (bicyclo-alkenyl)alkyl, or (tricycloalkyl)alkyl. Representative R groups include the following: allyl, 2-methylallyl, 1-ethyl-allyl, 3-methyl-2-butenyl, cis- and trans-2-butenyl, cis- and trans-3-methyl-2-pentenyl, 2,3-dimethyl-2-butenyl, 3-hexenyl, and 2-decenyl; cyclopropylmethyl, (1-methylcyclo-propyl)methyl, (cis- and trans-2-methylcyclopropyl)methyl, (cis, cis-, trans, cis- and trans,trans-2,3-dimethylcyclopropyl)-methyl, 1-cyclopropylethyl, 1-cyclopropylbutyl, cyclobutyl-methyl, cyclopentylmethyl, cyclohexylmethyl, 1-cyclohexylethyl and cycloheptylmethyl; (2,3-epoxypropyl), (cis- and trans-2,3-epoxybutyl), tetrahydrofurfuryl, (tetrahydropyranyl)methyl, 1-(tetrahydropyranyl)ethyl, 2,3-thioepoxypropyl, tetrahydro-thenyl, and (tetrahydrothiopyranyl)methyl; 2-propynyl, 1-methyl-2-propynyl and 1-ethyl-2-butynyl; (2,3-dimethylcyclopropenyl)-methyl, (2- and 3-cyclopentenyl)methyl, and (1-,2- and 3-cyclo-hexenyl)methyl; norbornylmethyl, norcarylmethyl, and (bicyclo-[2.2.2]octyl)-methyl; cis- and trans-2,4-pentadienyl, and cis,cis-, cis,trans-. trans,cis- and trans,trans-2,4-hexadienyl; (2,5-cyclohexadienyl)methyl, (cycloheptadienyl)methyl, (bicyclo-[2.21]heptenyl)methyl, (bicyclo[2.2.2]octenyl)methyl, and 1-and 2-adamantylmethyl.

It is well understood that the above groups are named only to illustrate, but not to limit, the invention; and that isomers not specifically named also are included. This means that the positions of substituents of double or triple bonds or of heteroatoms can be different from those specifically enumerated; and also that geometric isomers where not specified and all stereoisomers also are within the scope of the invention. Finally, mixtures of various isomers are possible and also are included. A skilled chemist can readily isolate any desired isomer from the mixture.

In addition to the free bases themselves, their addition salts with pharmaceutically acceptable organic or inorganic acids can be used. These salts have a considerably higher water solubility than the free bases and are thus more suitable for the preparation of aqueous solutions. Representative pharmaceutically acceptable acids which can be used to form 1,2,3,4,8,9-hexahydro-3-(substituted)pyrido[4', 3':2,3]indolo[1,7-ab][1]benzazepine derivative salts of the present invention are: hydrochloric, hydrobromic, sulfuric, sulfamic, phosphoric, nitric, maleic, fumaric, benzoic, ascorbic, citric, pamoic, succinic, methanesulfonic; ethanedisulfonic, acetic, oxalic, propionic, tartaric, salicylic, gluconic, lactic, malic, mandelic, cinnamic, citraconic, aspartic, stearic, palmitic, itaconic, glycolic, p-aminobenzoic, glutamic, and toluenesulfonic acids.

The novel compounds of formula (3) can be readily prepared by several routes. One of the possible reaction schemes could follow the process described in U.S. Pat. No. 3,457,271 wherein iminodibenzyl is converted to its N-nitroso derivative; the latter is reduced to N-aminoiminodibenzyl, which then is contacted with the proper N-substituted-4-piperidone; the resulting hydrazone is cyclized with an acid to the desired compound of formula (3). An alternative process starts with iminodibenzyl which is N-nitrosated, and the resulting N-nitroso derivative is contacted in the presence of acetic acid and zinc dust with the appropriate N-substituted-4-piperidone. The crude reaction product is then acidified with a strong acid and forms the desired compound of the general formula (3).

This reaction sequence also can start with N-nitrosoiminodibenzyl which is allowed to react with unsubstituted 4-piperidone in the presence of acetic acid and zinc dust; the crude reaction mixture is acidified to give the unsubstituted base (4). This compound can then be substituted on the tetrahydropyridino nitrogen. Still other routes to the novel compounds of formula (3) are possible but need not be described here. The preparation of representative novel compounds of the present invention is illustrated below by Examples 1–19, wherein all temperatures are given in degrees centigrade. Glass plates coated with a 0.25 mm. layer of silica gel containing fluorescent indicator F-254 (manufactured by E. Merck AG, Darmstadt) are used for thin layer chromatography.

EXAMPLE 1

1,2,3,4,8,9-hexahydropyrido[4', 3':2,3] indolo[1,7-ab][1]benzazepine (formula 4)

To a mixture of 4.5 g of N-nitrosoiminodibenzyl (5-nitroso-10,11-dihydro-5H-dibenz[b,f]azepine), 6.0 g. of 4-piperidone hydrochloride and 6.5 g. of zinc dust in 30 ml. of absolute ethanol 12 ml. of glacial acetic acid are added dropwise, with constant stirring. Occasional cooling in an icebath is required to maintain the temperature at 20°–25° during the course of the reaction. After a little over 4 hours, the unchanged zinc is filtered off, washed with a minimum of absolute ethanol, and to the combined filtrate and wash there is added with stirring 8 ml. of concentrated sulfuric acid in 50 ml. of absolute ethanol. Stirring is continued while the mixture is warmed for about ten minutes, until the alcohol begins to reflux. It is then cooled down again; the inorganic insolubles are filtered off, and approximately 500 ml. of water is added to the filtrate, resulting in a voluminous white precipitate. The whole mixture is extracted with ether, and the residual aqueous phase is warmed up to transform the precipitate into granular solids, which are then filtered off and redissolved in approximately 600 ml. aqueous acetic acid. Some warming is required to completely dissolve all material. On treating this solution with 3N aqueous ammonia, the title compound is obtained as a tan-white granular solid, m.p. 134°–137°.

EXAMPLE 2

3-isobutyl-1,2,3,4,8,9-hexahydropyrido-[4′,3′:2,3]indolo[1,7-ab ][1]benzazepine hydrochloride (salt of the compound of formula 3, where R = isobutyl)

To a solution of 5.5 g. of the product of Example 1 in 150 ml. of dichloromethane containing 25 ml. of triethylamine a solution of 4.2 ml. of isobutyryl chloride in approximately 25 ml. of dichloromethane is added dropwise, with constant stirring. On heating to reflux, the white precipitate originally formed redissolves. Refluxing is continued for 2 hours; the solution is cooled, washed with water and with saturated sodium bicarbonate, dried over anhydrous potassium carbonate, and stripped down to a dark gum, which is taken up in hexane, boiled and decolorized. After concentrating the clear solution tp 100 ml. and cooling, a gum separates which solidifies completely on standing. After 1 week, 1,2,3,4,8,9-hexahydropyrido[4′, 3′:2,3]indolo[1,7-ab][1]benzazepin isopropyl ketone, m.p. 122°–124°, is isolated.

A solution of 3.3 g. of this ketone in 50 ml. of tetrahydrofuran is added to a stirred suspension of 1.5 g. lithium aluminum hydride in 100 ml. of tetrahydrofuran, and the mixture is refluxed for four hours with continued stirring. It is then cooled and hydrolyzed with 1N sodium hydroxide and the aluminum salts are filtered off. The mother liquor is evaporated under reduced pressure, the resulting residue dissolved in ether, and after drying the ether is removed in vacuo. The residual oil is dissolved in a 1:1 mixture of ethyl acetate-benzene and chromatographed on a 14 × 2.2 cm. column of neutral alumina, activity I. The first 150 ml. fraction of eluate, which contains only a single substance as shown by thin layer chromatography, is taken down to dryness; the residual colorless oil is dissolved in ether, and a solid, somewhat gummy salt is precipitated by addition of an excess of ethereal hydrogen chloride. On trituration of the salt with acetone, 1,2,3,4,8,9-hexahydro-3-isobutylpyrido[4′,3′:2,3][1]benzazepine hydrochloride, m.p. 237°–240° , is obtained as a fine, white solid.

EXAMPLE 3

3-(cyclopropylmethyl)-1,2,3,4,8,9-hexahydropyrido[-4′,3′:2,3]indolo[1,7-ab][1]benzazepine (formula 3, R = cyclopropylmethyl)

A solution of 10.4 g. of cyclopropanecarbonyl chloride in 150 ml. of dichloromethane is rapidly added to a solution of 12.5 g. of 4-piperidone ethylene acetal (1,4-dioxa-8-azaspiro[4.5]decane) and 20 g. of triethylamine in 200 ml. of dichloromethane, causing the solution to reflux. Heating to reflux with stirring is continued overnight; the mixture is cooled and the precipitated triethylammonium chloride filtered off. The mother liquor is concentrated to about half volume, washed with water, dried over anhydrous potassium carbonate, and stripped to dryness. The residual oil quickly solidifies, and on crystallization from 300 ml. hexane yields cyclopropyl 1,4-dioxa-8-azaspiro[4.5]-dec-8-yl ketone, m.p. 72°–74°, as white needles. Reduction of 14.0 g. of this compound in 60 ml. freshly chromatographed, peroxide-free ether by dropwise addition to a suspension of 2.5 g. of lithium aluminum hydride in similarly treated ether, followed by three hours of refluxing, yields 8-(cyclopropylmethyl)-1,4-dioxa-8azaspiro[4.5]decane as a colorless oil. Hydrolysis of this ethylene acetal by refluxing in 2N hydrochloric acid, followed by basification with 50% sodium hydroxide, extraction into ether, drying of the extrct, and stripping off the solvent, yields a crude product which distills at 111°–122°/16 mm. to give 1-(cyclopropylmethyl)-4-piperidone, shown by gas-liquid chromatography to be 95–99% pure.

To a suspension of 3.8 g. of N-nitrosoiminodibenzyl and 5 g. of zinc dust in 30 ml. absolute alcohol, 5.7 g. of this piperidone is added, followed by 10.2 ml. glacial acetic acid, added dropwise with stirring and occasional cooling to maintain a temperature of 20°–25°C. After 8 hours, the unchanged zinc is filtered off and the mother liquor evaporated nearly to dryness. The residue is extracted with benzene; the extract is washed with a saturated sodium chloride solution, dried over magnesium sulfate, and evaporated. The residue is dissolved in 50 ml. of ethanol, treated with a solution of 8 ml. of concentrated sulfuric acid in 50 ml. of ethanol, and heated on a steam bath for about ten minutes. The solution is poured into cold water, made basic with concentrated sodium hydroxide, and extracted with ether. The ether extract yields on evaporation 3-(cyclopropylmethyl)-1,2,3,4,8,9-hexahydropyrido[4′,3′:2,-3]indolo[1,7-ab][1]benzazepine, which is recrystallized from 6:1 acetone-water by volume to give the pure material, m.p. 94°–96°C.

On addition of a solution of 10.5 g. of methane sulfonic acid in 20 ml. acetone to a solution of 36 g. of the above base in 200 ml. acetone, an exothermic reaction occurs, from which the salt separates while the reaction mixture is still hot. Further recrystallization of this salt from 1:1 hexane-isopropanol yields 3-(cyclopropylmethyl)-1,2,3,4,8,9-hexahydropyrido[4′,3′:2,3]indolo[1,7-ab][1]benzazepine methanesulfonate, m.p. 220°–221°, a crystalline, white solid which is better than 50% soluble in water.

EXAMPLE 4

3-(2-butynyl)-1,2,3,4,8,9-hexahydropyrido[4',3':2,3]indolo[1,7-ab][1]benzazepine hydrochloride (salt of the compound of Formula 3 where R = 2-butynyl)

By the procedure of Example 3, using instead of 1-(cyclopropylmethyl)-4-piperidone an equimolar amount of 1-(2-butynyl)-4-piperidone,3-(2-butynyl)-1,2,3,4,8,9-hexahydropyrido[4',3':2,3]indolo[1,7-ab][1]-benzazepine hydrochloride is obtained as a microcrystalline white solid, which after drying at 100°/0.5 mm for four hours starts to sinter at about 170° and then melts with decomposition at 173°–175°.

EXAMPLE 5

3-(cyclopropylmethyl)-1,2,3,4,8,9-hexahydropyrido[-4',3':2,3]indolo[1,7-ab][1]benzazepine hydrochloride (salt of the compound of formula 3 where R = cyclopropylmethyl)

To a solution of 16.4 g. of the product of Example 1 in 500 ml. of dichloromethane, 7.3 g. of cyclopropanecarbonyl chloride is added, followed by dropwise addition of 10 ml. of triethylamine. A mildly exothermic reaction takes place, after which stirring of the mixture is continued at room temperature overnight. The mixture is then washed with 1N hydrochloric acid and water, and dried over anhydrous sodium carbonate. On evaporation to dryness, crude cyclopropyl 1,2,3,4,8,9-hexahydropyrido[4',3':2,3]indolo[1,7-ab][1]benzazepin-3-yl ketone is obtained as a glassy product, m.p. 149°–152° on recrystallization from ethanol. A solution of 8.6 g. of this material in 120 ml. of tetrahydrofuran is added dropwise to a suspension of 2.3 g. of lithium aluminum hydride in 180 ml. of tetrahydrofuran. On completion of the addition, the mixture is first refluxed for 4 hours, then allowed to stir at room temperature overnight and finally decomposed in the usual manner. After filtering off the inorganic salts, the filtrate is dried over anhydrous sodium carbonate, evaporated in vacuo; the residue is dissolved in a 1:1 mixture of ethyl acetate-benzene and chromatographed on a 14 × 2.2 cm. column of basic alumina, activity I. The eluate is taken down to dryness; the residual oil dissolved in absolute alcohol, saturated with ethanolic hydrogen chloride, and once again evaporated to dryness. Upon crystallization of the residue from acetone, 3-(cyclopropylmethyl)-1,2,3,4,8,9-hexahydropyrido[4',3':2,3]indolo[1,7-ab][1]benzazepine hydrochloride, m.p. 267°, is obtained.

EXAMPLES 6–16

In a like manner, but using in place of cyclopropanecarbonyl chloride an equimolar amount of
cyclobutanecarbonyl chloride,
cyclopentanecarbonyl chloride,
cyclohexanecarbonyl chloride,
exo-7-norcaranecarbonyl chloride,
1-adamantanecarbonyl chloride
2-adamantanecarbonyl chloride,
3-cyclohexene-1-carbonyl chloride,
2,3-dimethyl-2-cyclopropene-1-carbonyl chloride,
cis-1,6-dimethyl-endo-3-norcarene-7-carbonyl chloride,
4-methylbicyclo[2.2.2] octane-1-carbonyl chloride,
4-methylbicyclo [2.2.2] oct-2-ene-1-carbonyl
respectively, the following products are obtained:

6. 3-(cyclobutylmethyl)-1,2,3,4,8,9-hexahydropyrido[-4',3':2,3]indolo[1,7-ab][1]benzazepine hydrochloride, m.p. 256°–258° after recrystallization from acetone;

7. 3-(cyclopentylmethyl)-1,2,3,4,8,9-hexahydropyrido[4',3':2,3]indolo[1,7-ab][1]benzazepine hydrochloride, m.p. 227°–229° after trituration with acetone;

8. 3-(cyclohexylmethyl)-1,2,3,4,8,9-hexahydropyrido[4',3':2,3]indolo[1,7-ab][1]benzazepine hydrochloride, m.p. 227° after trituration with acetone, drying in a vacuum oven to a vitreous solid, powdering the latter, and repeating the cycle of redrying and repowdering;

9. 3-(exo-7-norcarylmethyl)-1,2,3,4,8,9-hexahydropyrido[4',3':2,3]indolo[1,7-ab][1]benzazepine hydrochloride, as the monoacetonate, m.p. 189°–192° (dec.) after recrystallization from acetone;

10. 3-(1-adamantylmethyl)-1,2,3,4,8,9-hexahydropyrido[4',3':2,3]indolo[1,7-ab][1]benzazepine hydrochloride, m.p. 278° after recrystallization from ethanol 11. 3-(2-adamantylmethyl)-1,2,3,4,8,9-hexahydropyrido[4',3':2,3]indolo[1,7-ab][1]benzazepine hydrochloride 12. 3-[(3-cyclohexen-1-yl)methyl]-1,2,3,4,8,9-hexahydropyrido[4',3':2,3]indolo[1,7-ab][1]benzazepine hydrochloride, m.p. 198°–200° after recrystallization from acetone.

13. 3-[(2,3-dimethyl-2-cyclopropen-1-yl)methyl]-1,2,3,4,8,9-hexahydropyrido[4',3':2,3]indolo[1,7-ab][1]benzazepine hydrochloride, m.p. 193°–194° (dec.) after drying at 100°/0.05 mm.

14. 3-[cis-1,6-dimethyl-endo-3-norcaren-7-yl)methyl]-1,2,3,4,8,9-hexahydropyrido[4',3':2,3]indolo[1,7-ab][1]benzazepine, m.p. 141°–143° after recrystallization from hexane 15. 1,2,3,4,8,9-hexahydro-3-[(4-methylbicyclo[2.2.2]oct-1-yl)methyl]pyrido[4',3':2,3]indolo[1,7-ab][1]benzazepine hydrochloride 16. 1,2,3,4,8,9-hexahydro-3-[(4-methylbicyclo[2.2.2]oct-2-en-1-yl)methyl]pyrido[4', 3':2,3]indolo[1,7-ab][1]benzazepine hydrochloride

EXAMPLE 17

3-[(cis,cis-2,3-dimethylcyclopropyl)methyl]-1,2,3,4,8,9-hexahydropyrido[4',3':2,3]indolo[1,7-ab][1]benzazepine hydrochloride [salt of compound of Formula 3 where R = (cis,cis-2,3-dimethylcyclopropyl)methyl]

A solution of 2.7 g. of the product of Example 13 in 75 ml. of ethanol is hydrogenated over 150 mg. of $PtO_2$ at room temperature and 25 p.s.i. Hydrogen uptake is rapid and completed in 5 minutes. The catalyst is removed by filtration through a bed of celite and the filtrate evaporated to dryness. The residue is boiled with anhydrous ether and again filtered. After drying at 100°/0.1 mm. for 2 hours, the title compound is obtained as a pale yellow powder with a somewhat indefinite melting point of 170°–174° (dec.).

EXAMPLE 18

1,2,3,4,8,9-hexahydro-3-[(trans-2-methylcyclopropyl)methyl]pyrido[4',3':2,3]indolo[1,7-ab][1]benzazepine hydrochloride [salt of compound of Formula 3 where R = (2-methylcyclopropyl)methyl]

Similarly, but using in place of the cyclopropane carbonyl chloride an equimolar amount of a mixture of cis- and trans- 2-methylcyclopropanecarbonyl chloride, a yellow gum, consisting of a mixture of 1,2,3,4,8,9-hexahydropyrido [4',3':2,3]indolo[1,7-ab][1]benzazepin-1-yl cis- and trans-2-methylcyclopropyl ketones, is obtained. Without separation or purification, this mixture is reduced with lithium aluminum hydride in tetrahydrofuran; and the free base, dissolved in benzene, is chromatographed on a 21 × 2.4 cm. column of neutral alumina, activity I. On evaporation of the eluate, a pale yellow oil is obtained, which is dissolved in ether and treated with ethereal hydrogen chloride. The resulting salt is dried to give the title compound, m.p. ~250° (dec.). — Thin layer chromatography, using an 8% solution of diethylamine in benzene as eluent, show this product to move as a single spot; the cis-isomer of the precursor is apparently reductively cleaved during the lithium aluminum hydride reduction.

EXAMPLE 19

1,2,3,4,8,9-hexahydro-3-[(1-methylcyclopropyl)methyl]pyrido[4',3':2,3]indolo[1,7-ab][1]benzazepine hydrochloride [salt of compound of Formula 3 where R = (1-methylcyclopropyl)methyl]

Starting with 1-methylcyclopropanecarbonyl chloride and following the procedure of Example 5, 1,2,3,4,8,9-hexahydropyrido[4',3':2,3]indolo[1,7-ab][1]benzazepin-3-yl 1-methylcyclopropyl ketone is obtained as a dark oil which gradually solidifies. Without further purification, a solution of 5.6 g. of this solid in 50 ml. benzene is added to a solution of 7 ml. of Vitride™ (70% solution of sodium bis(2-methoxyethoxy)aluminum hydride, NaAlH$_2$(OCH$_2$CH$_2$OCH$_3$)$_2$, in benzene) in 50 ml. benzene, and after the intial exothermic reaction has subsided, the mixture is heated, under nitrogen, to reflux for 75 minutes. It is then cooled, decomposed with water; the inorganic precipitates are filtered off; and the benzene solution is washed with water and dried over anhydrous potassium carbonate. It is then filtered through a column of basic alumina, activity I. On evaporation of the eluate, a pale yellow oil is obtained, which is dissolved in ether and treated with ethereal hydrogen chloride to give the title compound, m.p. 172°–177° after drying at 100°/0.3 mm

EXAMPLE 20

3-(1-cyclopropylethyl)-1,2,3,4,8,9-hexahydropyrido[4',3':2,3]indolo[1,7-ab][1]benzazepine hydrochloride (salt of compound of Formula 3 where R = 1-cyclopropylethyl)

A mixture of 5.5 g. of the product of Example 1, 2.3 g. of (1-chloroethyl)cyclopropane and 3.0 g. of sodium bicarbonate in 100 ml. of dimethylformamide is heated to 70°, with continued stirring, overnight, and the reaction mixture is then poured into water and extracted with ether. The extract is dried, evaporated to dryness, and the residue is dissolved in benzene and chromatographed. The eluate is then evaporated to dryness, the residue dissolved in absolute alcohol, treated with alcoholic hydrogen chloride, stripped down to dryness, and the glassy residue triturated with acetone to yield white crystals of the title compound, m.p. 249°–252°.

EXAMPLE 21

1,2,3,4,8,9-hexahydro-3-(tetrahydrofurfuryl)pyrido[4',3':2,3]indolo[1,7-ab][1]benzazepine hydrochloride (salt of compound of Formula 3 wherein R = tetrahydrofurfuryl)

By a procedure similar to that of Example 12 but using 3.6 g. of 2-(bromomethyl)tetrahydrofuran in place of the (1-chloroethyl)cyclopropane, and heating to mild reflux for 105 minutes, an oily product is obtained, which on trituration with ethanol-ether yields a crystalline product, m.p. 213°–217°. On recrystallization from ethanol-ether, followed by drying for five hours at 100°, the title compound m.p. 215°–218°, is obtained.

EXAMPLE 22

3-cyclopropyl-1,2,3,4,8,9-hexahydropyrido[4',3':2,3]indolo[1,7-ab][1]benzazepine hydrochloride (salt of compound of Formula 3 where R = cyclopropyl)

A mixture of 28.5 g. of cyclopropylamine and 100 g. of ethyl acrylate is stirred at room temperature for 20 hours, and from the reaction mixture diethyl 3,3'-(cyclopropylimino) dipropionate is distilled, b.p. 122°–124° at 0.8 mm Hg. A solution of 21.3 g. of this diester in 30 ml. benzene is added dropwise to a cooled suspension of 8.0 g. of sodium hydride in 150 ml. benzene to which 5 ml. ethanol have been added. Soon an exothermic reaction starts, which at first requires occasional cooling, and after heat evolution subsides, the reaction is allowed to stand at room temperature overnight. The next morning it is heated on a steam bath for 1 hour, cooled, and decomposed with 20 g. acetic acid and 13.5 g. water. After filtering off the solids, the benzene solution is washed with aqueous bicarbonate, dried over anhydrous sodium sulfate, and stripped to dryness. On cooling the oily product in the refrigerator for three days and triturating with hexane, crystalline ethyl 1-cyclopropyl- 3-oxo-3-piperidinecarboxylate is obtained. After refluxing 17.8 g. of this ester in 90 ml. of 6N hydrochloric acid for one hour, and taking the resulting solution down to dryness, the solid residue is triturated with hot isopropyl alcohol to yield 1-cyclopropyl-4-piperidone hydrochloride, m.p. 209°–210°.

A mixture of 2.5 g. of N-aminoiminodibenzyl hydrochloride and 2.1 g. of the above piperidone in 25 ml. ethanol is heated on the steam bath for 15 minutes and cooled; a solution of 2 g. of concentrated sulfuric acid in 25 ml. of ethanol is added. An exothermic reaction takes place, after which the reaction mixture is heated for 10 more minutes on a steam bath, and poured into water. The resulting turbid suspension is basified with aqueous ammonia, and the resulting solid is taken up in ether. After further extractions with ether, the combined extracts are dried; the solvent is evaporated; and the residue is dissolved in ethanol and treated with ethanolic hydrogen chloride. The solvent is once again evaporated, and the remaining salt is crystallized from ethyl acetate-ether, and recrystallized from acetone-ether, to yield 3-cyclopropyl-1,2,3,4,8,9-hexahydropyrido[4',3':2,3]indolo[1,7-ab][1]benzazepine hydrochloride m.p. 218°–220°.

EXAMPLE 23

3-allyl-1,2,3,4,8,9-hexahydropyrido[4',3':2,3]indolo[1,7-ab][1]benzazepine (formula 3, R = allyl)

A mixture of 3.3 g. of the product of Example 1, 1.45 g. of freshly distilled 3-bromopropene and 1.7 g. of sodium bicarbonate is stirred at room temperature, for 24 hours, in 50 ml. dimethylformamide. At the end of this period, the mixture is poured into water, extracted with ether, and the combined extracts are dried and stripped down. The residue is dissolved in benzene, and the resulting solution chromatographed through a column of neutral alumina. The oily residue obtained on stripping down the eluate is recrystallized from isopropyl alcohol to yield 3-allyl-1,2,3,4,8,9-hexahydropyrido[4',3':2,3]indolo[1,7-ab][1]benzazepine m.p. 112°–113°.

EXAMPLES 24–27

By a similar procedure, but using instead of 3-bromopropene an equivalent amount of
3-chloro-2-methylpropene
trans-1-chloro-2-butene
1-chloro-3-methyl-2-butene
3-bromopropyne
respectively, the following products are obtained:

24. 1,2,3,4,8,9-hexahydro-3-(2-methylallyl)pyrido[4',3':2,3]indolo[1,7-ab][1]benzazepine hydrochloride, m.p. 235°–237° after recrystallization from isopropanol-ether;
25. 3-(trans-2-butenyl)-1,2,3,4,8,9-hexahydropyrido[4',3':2,3]indolo[1,7-ab][1]benzazepine hydrochloride, m.p. 140°–143°;
26. 1,2,3,4,8,9-hexahydro-3-(3-methyl-2-butenyl)-pyrido[4',3':2,3]indolo[1,7-ab][1]benzazepine hydrochloride, m.p. 143°–146°;
27. 1,2,3,4,8,9-hexahydro-3-(2-propynyl)pyrido[4',3':2,3]indolo[1,7-ab][1]benzazepine hydrochloride, m.p. 145°–148° after trituration of the crude product with ethanol-ether followed by vacuum drying at 100° for 5 hours.

The compounds of the present invention, when administered to warm-blooded animals in effective psychotropic doses, do not produce certain of the undesirable side effects commonly associated with prior art central nervous system depressants, such as ataxia. Of particular interest are those compounds which possess both minor and major tranquilizer activities. These compounds are not likely to cause addiction when abused because the resulting major tranquilizer effect would be considered very undesirable by the subject. Indeed, it is well known that major tranquilizers are not subject to abuse. The preferred compounds of the present invention are those in which the $R_2$ group is cyclopropylmethyl, (1-methylcyclopropyl)methyl, and 2-methylallyl, as well as their addition salts with pharmaceutically acceptable acids. These compounds have remarkable minor tranquilizer activities as compared with their close structural analogs in which the $R_2$ group is isobutyl or cyclopropyl.

The pharmacological evaluation of the novel compounds of this invention shows that they exhibit typical major tranquilizer activity as evidenced by dose-dependent antagonism of amphetamine hyperactivity in mice, antagonism of apomorphine and amphetamine stereotypy in rats, blockade of conditioned avoidance responses (C.A.R.) in mice and rats, and taming of rhesus monkeys. In those compounds which also exhibit minor tranquilizer activity, antagonism of an approach-avoidance ("conflict") situation in rats and decreased fear and increased approach-behavior in the rhesus monkeys are observed. The techniques employed in the pharmacological evaluation of the novel compounds of the present invention are described below, each one preceded by the abbreviation used at the head of the column of the following Table in which the quantitative results are listed:

Screen

Results given in: mg/kg po/mouse
Mouse Screen: The minimal effective dose (MED) is the lowest oral dose producing an obvious decrease in locomotor activity, using observational techniques. Groups of 3 mice are given decreasing oral doses at 0.5 log intervals (300, 100, 30 . . . etc.) until no behavioral effects are evident. Decrease of locomotor activity is indicative of general central nervous system depressant activity.

A.A.

Results given in: mg/kg po/mouse
Mouse Anti-Amphetamine Activity: Groups of 5 mice are given d-amphetamine sulfate 5 mg/kg sc 1 hour after oral administration of graded doses of test compound. The mice are placed in photocell activity units immediately after amphetamine administration and locomotor activity is recorded for 60 minutes. The $ED_{50}$ is calculated as the dose causing a 50% reduction in locomotor activity relative to the activity of the amphetamine-treated control mice. Amphetamine antagonism at non-toxic doses appears to correlate with major tranquilizer activity in man.

C.A.R

Results given in: mg/kg po/mouse mg/kg po/rat
Mouse and Rat Conditioned Avoidance Response: Mice and rats are trained to jump out of a pit onto a ledge to avoid shock when presented with a light and sound conditioned stimulus. The animals are tested 1, 2, and 4 hours after administration of the test compound. Three to 4 dose levels and groups of 4–8 animals/dose are used. The $ED_{50}$ is the dose producing a block of the C.A.R. in 50% of the animals. Blocking of the C.A.R. at non-toxic doses appears to correlate with major tranquilizer activity in man.

C.A.R.

Results given in: mg/kg po/dog
Dog Conditioned Avoidance Response: Dogs are trained to raise a forelimb when presented with a conditioned stimulus (light) in order to avoid an electric shock. Blocks of 10 trials are given to groups of four dogs during a pretreatment period and at 1, 2, and 4 hours after oral administration of test compound. The $ED_{50}$ values are calculated as the dose causing 50% of the animals to show five or more incorrect responses. Blocking of the C.A.R. at non-toxic doses appears to correlate with major tranquilizer activity in man.

Taming

Results given in: mg/kg po/monkey

Rhesus Monkey Taming Effects: Compounds are administered orally to groups of six rhesus monkeys. The behavior of the animals is then evaluated by observational means. Taming effects are determined by the ability of the observer to approach and touch the monkey. Compounds with major tranquilizer activity in man can produce a state of passive tameness in the rhesus monkey wherein it can be touched without provoking any of the threatening or aggressive behavior seen in the normal animal. The MED is the minimal oral dose at which some taming effect can be observed.

Conflict

Results given in: mg/kg po/rat

Rat Conflict (Approach-Avoidance) Test: Food deprived rats are trained to pass from one compartment to an adjacent one to obtain food. The training consists of three exposures to the test situation on day one of the experiment. The rats are given limited (1–2 hr) free access to food in their home cages on day one and are then food deprived for at least 18 hours. On day two of the experiment, the rats are given a control exposure to the test situation followed by a second exposure after ½ to 1 hour in which they are shocked after crossing and eating. Groups of 6–8 rats are then dosed orally with solvent or test compound and then reexposed to the test situation after 1 or 2 hours.

Compounds showing minor tranquilizer (anxiolytic) activity in man such as diazepam and meprobamate produce an apparent decreased fear in the test animals so that they cross to obtain food despite having received a shock earlier. This effect is dose-related (and the MED is the minimum dose at which this effect is obtained); rats dosed with solvent only consistently show a high level of fear as evidenced by decreased mobility and absence of feeding when placed in the test situation after receiving a shock.

Approach

Results given in: mg/kg po/monkey

Rhesus Monkey Approach Effects: Compounds are administered orally to groups of six rhesus monkeys. The behavior of the animals is then evaluated by observational means. Approach effects are examined by determining whether a monkey shows decreased fear as evidenced by reaching out for food or objects or coming closer instead of the withdrawal behavior that is seen in the untreated monkey. Compounds influencing this type of behavior have been shown to be useful in man as minor tranquilizer (anxiolytic) agents. The MED is the oral dose at which the animals show signs of decreased fear.

Quantitative results obtained with representative compounds of the present invention, using the methods described above, are listed in the following Table, which includes also results obtained with chlorpromazine (No. 21), a well-known major tranquilizer, and with diazepam (No. 22), a well-known minor tranquilizer, for basis of comparison. Further, two compounds structurally related but not within the scope of this invention, are also included; they are the 3-isobutyl (No. 1) and the 3-cyclopropyl (No. 2) analogs of the compounds of the present invention.

| No. | R | 3-R-1,2,3,4,8,9-HEXAHYDROPYRIDO[4',3':2,3]INDOL[1,7-ab][1]BENZAZEPTNES | | | | | | | |
|---|---|---|---|---|---|---|---|---|---|
| | | Exmpl. | Screen (mouse) MED | A.A. (mouse) ED$_{50}$ | C.A.R. (mouse) ED$_{50}$ | C.A.R. (rat) ED$_{50}$ | C.A.R. (dog) ED$_{50}$ | Taming (monkey) MED | Conflict (rat) MED | Approach (monkey) MED |
| 1. | —C—C(C)(C) | 2 | 10–30 | 10 | >40 | >40 | * | 20–30 | >40 | * |
| 2. | cyclopropyl | 22 | 100–300 | >100 | * | >40 | * | >20 | >40 | * |
| 3. | —C-cyclopropyl | 3,5 | 30–100 | 6 | 20 | 40 | >20 | 3–10 | 10–20 | 1–3 |
| 4. | —C-(cyclopropyl-C) | 18 | 10–30 | 6 | 10–30 | * | >40 | 1–3 | >40 | * |
| 5. | —C-(cyclopropyl with C) | 19 | 10–30 | 3–10 | 10–30 | * | 10–20 | 10–30 | 10–20 | * |
| 6. | —C-cyclobutyl | 6 | 10–30 | 20 | 6 | 4 | 20 | 1–3 | >40 | * |
| 7. | —C-cyclopentyl | 7 | 3–10 | 2 | 20 | 30 | 6 | 1–3 | >40 | * |
| 8. | —C-cyclohexyl | 8 | 3–10 | 2 | 20 | 30 | 10 | 1–3 | >40 | * |

-continued

3-R-1,2,3,4,8,9-HEXAHYDROPYRIDO[4',3':2,3]INDOL[1,7-ab][1]BENZAZEPTNES

| No. | R | Exmpl. | Screen (mouse) MED | A.A. (mouse) $ED_{50}$ | C.A.R. (mouse) $ED_{50}$ | C.A.R. (rat) $ED_{50}$ | C.A.R. (dog) $ED_{50}$ | Taming (monkey) MED | Conflict (rat) MED | Approach (monkey) MED |
|---|---|---|---|---|---|---|---|---|---|---|
| 9. | 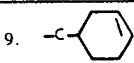 | 12 | 10–30 | 3–10 | 10–30 | * | * | 10 | * | * |
| 10. | 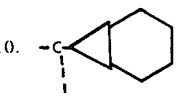 | 9 | 3–10 | 1 | 1–3 | 6 | * | 1–3 | >40 | * |
| 11. | 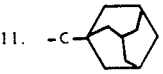 | 10 | 100–300 | >100 | 30 | >40 | * | * | * | * |
| 12. | 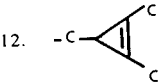 | 13 | 3–10 | 5 | * | * | * | * | * | * |
| 13. | 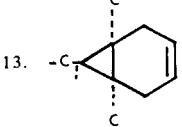 | 14 | 10–30 | * | * | * | * | * | * | * |
| 14. | 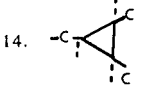 | 17 | 1–3 | * | * | * | * | * | * | * |
| 15. | 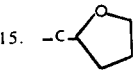 | 21 | 10–30 | 3–10 | 10–30 | * | * | >10 | * | * |
| 16. | 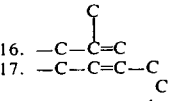 | 24 | 100–300 | 60 | 30–60 | 30 | >10 | 20 | 10–20 | * |
| 17. | —C—C=C—C | 25 | 10–30 | 20 | 20 | * | * | >20 | * | * |
| 18. | 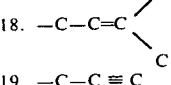 | 26 | 10–30 | 6 | 20 | * | * | 3–10 | >40 | * |
| 19. | —C—C≡C | 27 | 10–30 | 30–100 | 20 | * | * | * | * | * |
| 20. | —C—C≡C—C | 4 | 30–100 | * | * | * | * | * | * | * |
| 21. | chlorpromazine | — | 3–10 | 5 | 5 | 10 | 6 | 10–30 | 1 | 1 |
| 22. | diazepam | — | 3–10 | ic | Ia | Ia | 1 | 1 | 3–10[a] | 3–10[a] |

*indicates compound has not been evaluated in this test
[a]active, but also causes ataxia at this dose
I—inactive
Ia—inactive at doses not producing ataxia
ic—inconsistent results Free amine compounds of formula 3 are substantially insoluble in water. They are best administered orally at a level of about 0.3 to about 30 mg. per kilogram of body weight of the animal. At the lower doses, up to approximately 10 mg. per kilogram of body weight, a compound may exhibit minor tranquilizer activity, whereas at higher doses major tranquilizer activity predominates.

Addition salts of the compounds having formula 3 with pharmaceutically acceptable inorganic or organic acids are water-soluble and can be administered by subcutaneous or intramuscular injection. The dosage employed in such cases would be lower and generally would be within the range of 0.1 to 10 milligrams per kilogram of body weight. The usual dosage for minor tranquilizer activity is 0.3 to 10 mg/kg per os and for major tranquilizer activity 1 to 30 mg/kg per os. The relatively broad overlap between the minor tranquilizer and major tranquilizer ranges is due to differences among various animal species. The compounds of the present invention can be formulated into compositions comprising a compound of Formula 3 or a pharmaceutically acceptable acid addition salt thereof together with a pharmaceutically acceptable carrier. The carrier may be either a solid or liquid, and the compositions can be in form of tablets, liquid-filled capsules, dry filled capsules, aqueous solutions, nonaqueous solutions, suppositories, syrups, suspensions, and the like. The compositions can and in many cases do contain suitable preservatives, coloring, and flavoring agents. Some examples of the carriers which can be used in the preparation of the products of the invention are gelatin capsules, sugars such as lactose and sucrose; starches, dextrans, and cellulosics such as methyl cellulose and cellulose acetate phthalate; gelatin; talc; stearic acid salts; vegetable oils such as peanut oil, cottonseed oil, sesame oil, olive oil, corn oil and oil of theobroma; liquid petrolatum; polyethylene glycol; glycerine; sorbitol; propylene glycol; ethanol; agar; water and isotonic saline.

In preparing the compositions of the invention for pharmaceutical uses, the conventional practices and precautions are used. The composition intended for parenteral administration must be sterile, and this can be accomplished either by using sterile ingredients and carrying out the production under aseptic conditions, or by sterilizing the final composition by one of the usual procedures such as autoclaving under appropriate temperature and pressure conditions. Customary care should be exercised that no incompatible conditions exist between the active components and the diluent preservative or flavoring agent or in the conditions employed in preparation of the compositions.

The compositions of the invention can be introduced into warm-blooded animals by the oral, rectal or parenteral route. This can be done by swallowing, in the case of liquid or solid preparations; by suppositories; or by injecting the liquid preparations intravenously, intramuscularly, intraperitoneally, or subcutaneously.

Typical formulations of the type listed above which may be used for the administration of these compounds are:

Example A

| Ingredients | mg./tablet |
|---|---|
| 3-(cyclopropylmethyl)-1,2,3,4,8,9-hexahydropyrido[4′,3′:2,3]indolo[1,7-ab][1]-benzazepine hydrochloride | 15 mg. |
| lactose, USP | 183 mg. |
| magnesium stearate, USP | 2 mg. |
| color (if desired) | q.s. |

All of the above ingredients are passed through a suitable sieve, blended for 20 minutes, and compressed directly into tablets of 200 mg. on a suitable table press using a 11/32 inch punch and die.

Example B

| Ingredients | mg./tablet |
|---|---|
| 3-(exo-7-norcarylmethyl)-1,2,3,4,8,9-hexahydropyrido[4′,3:2,3]indolo[1,7-ab][1]-benzazepine hydrochloride | 50 mg. |
| lactose, USP | 215 mg. |
| methylcellulose, USP | 15 mg. |
| talc, USP | 6 mg. |
| starch, USP | 10 mg. |
| magnesium stearate, USP | 4 mg. |

Example B-continued

| Ingredients | mg./tablet |
|---|---|
| color (if desired) | q.s. |

The lactose and active ingredient are wet granulated with a solution of methylcellulose in a blender until a satisfactory mass is achieved. The mass is dried and classified through an appropriate sieve. The remaining ingredients are passed through an 80 mesh sieve and blended with the dried granulated material. The blend is then compressed into tablets on a suitable tablet press at a weight of 300 mg. using a ⅜ inch punch and die.

Example C

| Ingredients | mg./capsule |
|---|---|
| 1,2,3,4,8,9-hexahydro-3-(2-methylallyl)-pyrido[4′,3′:2,3]indolo[1,7-ab][1]-benzazepine hydrochloride | 25 mg. |
| lactose, USP | 100 mg. |
| magnesium stearate, USP | 1 mg. |
| colloidal silicon dioxide, N.F. | 2 mg. |

The combind ingredients are blended and passed through a 40-mesh sieve, and the mixture is encapsulated into a two-piece hard gelatin No. 3 capsule on a suitable encapsulating machine at a net weight of 128 mg.

Example D

| Ingredients | gram/liter |
|---|---|
| 1,2,3,4,8,9-hexahydro-3-(2-methylallyl)pyrido-[4′,3′:2,3]indolo[1,7-ab][1]benzazepine methanesulfonate | 3 g. |
| granulated sugar | 600 g. |
| sodium benzoate | 1 g. |
| flavor | q.s. |
| color | q.s. |
| deionized water | q.s. |

All of the above ingredients are dissolved in water and made up to a volume of one liter.

Example E

| Ingredients | gram/liter |
|---|---|
| 3-(cyclopropylmethyl)-1,2,3,4,8,9-hexahydro-pyrido[4′,3′:2,3]indolo[1,7-ab][1]benzazepine methanesulfonate | 10 g. |
| propylparaben, USP | 0.2 g. |
| methylparaben, USP | 1.8 g. |
| Water for Injection | q.s. to 1 liter |

Dissolve the parabens in about 800 ml. of Water for Injection at 80°. Cool to room temperature, add the active ingredient, and stir to dissolve. If the solution is aseptically prepared, sterile filtration through a millipore filter or other suitable retentive filter is desirable. Terminal sterilization by autoclaving may also be employed to render the product sterile.

Example F

| Ingredients | gram/liter |
|---|---|
| 3-[(2-cyclohexen-1-yl)methyl]-1,2,3,4,8,9-hexahydropyrido[4′,3′:2,3]indolo[1,7-ab]-[1]benzazepine hydrochloride | 10 g. |
| propylparagen, USP | 0.2 g. |
| methylparaben, USP | 1.8 g. |
| sodium carboxymethylcellulose, USP (CMC) | 5 g. |
| polysorbate 80, USP | 1 g. |

Example F-continued

| Ingredients | gram/liter |
| --- | --- |
| Water for Injection | q.s. to 1 liter |

The parabens, CMC and one-half of the polysorbate 80 are dissolved in about 700 ml. of Water for Injection, with agitation at 80° (solution A). A slurry is made of the active ingredient, one-half of the polysorbate 80 and about 200 ml. of Water for Injection (slurry B). Solution A is aseptically filtered through a Millipore filter to render it sterile, while slurry B is autoclaved for 30 minutes at 15 lbs. steam pressure to make it sterile. A and B are aseptically combined, brought to correct volume with sterile Water for Injection, and mixed to homogeneity.

I claim:

1. A compound selected from (A) a free base having the formula

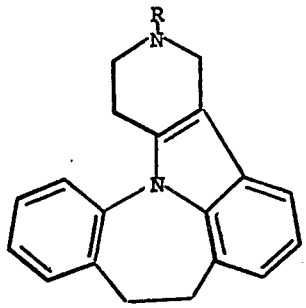

in which R is $C_nH_{(2n-x)}Z_y$, wherein:
  $n$ is a positive integer of 3-12;
  $x$ is 1, 3, or 5;
  $y$ is 0 or 1; and
  $Z$ is oxygen or sulfur;
with the proviso that when $y$ is 1, $n$ is no larger than 6, and $x$ is 1; and when $x$ is 5, $n$ is at least 7; and (B) an addition salt of (A) with a pharmaceutically acceptable acid.

2. A compound of claim 1 in which R is (cycloalkyl)alkyl.
3. A compound of claim 1 in which R is alkenyl.
4. A compound of claim 1 in which R is alkynyl.
5. A compound of claim 1 in which R is (alkylcycloalkyl)methyl.
6. A compound of claim 1 in which R is (cycloalkenyl)methyl.
7. A compound of claim 1 in which R is (bicycloalkyl)methyl.
8. A compound of claim 1 in which R is (oxacycloalkyl)methyl.
9. A compound of claim 2 in which R is cyclopropylmethyl.
10. A compound of claim 3 in which R is 2-methylallyl.
11. A compound of claim 5 in which R is (1-methylcyclopropyl)methyl.
12. A compound of claim 7 in which R is exo-7-norcarylmethyl.

* * * * *